United States Patent [19]

Toth

[11] Patent Number: 4,508,831

[45] Date of Patent: Apr. 2, 1985

[54] ANTI-STREPTOLYSIN O LATEX REAGENT AND PROCESS FOR THE PREPARATION THEREOF

[75] Inventor: Tibor Toth, Marburg, Fed. Rep. of Germany

[73] Assignee: Behringwerke Aktiengesellschaft, Fed. Rep. of Germany

[21] Appl. No.: 476,128

[22] Filed: Mar. 17, 1983

[30] Foreign Application Priority Data

Mar. 19, 1982 [DE] Fed. Rep. of Germany ....... 3210080

[51] Int. Cl.³ ............................................ G01N 33/54
[52] U.S. Cl. ...................................... 436/512; 435/7; 436/533; 436/534; 436/811; 436/815
[58] Field of Search ........................ 436/533, 534, 512

[56] References Cited

U.S. PATENT DOCUMENTS 3,992,631 11/1976 Harte .............................. 436/815 X
4,088,749 5/1978 Grundman .......................... 436/533
4,148,609 4/1979 Ricci ............................... 436/815 X
4,329,151 5/1982 Lou .

OTHER PUBLICATIONS

Chemical Abstracts, 73: 1975r (1970).

Primary Examiner—Sidney Marantz
Attorney, Agent, or Firm—Finnegan, Henderson, Farabow, Garrett & Dunner

[57] ABSTRACT

A process for the preparation of an antistreptolysin O latex reagent and the reagent produced by such process. The reagent is prepared by reacting streptolysin O with a bifunctional low molecular weight compound and, in the preferred embodiment, with a gamma globulin or a Fab fragment thereof to form a product, which product is adsorbed to latex particles. The reagent is stable and may be used for the determination of antibodies to streptolysin O.

20 Claims, No Drawings

ANTI-STREPTOLYSIN O LATEX REAGENT AND PROCESS FOR THE PREPARATION THEREOF

The invention provides a latex reagent for the determination of antibodies against streptolysin O, and a process for the preparation of this reagent.

Streptolysin O is an exocellular product of the metabolism of β-hemolytic streptococci of the Lancefield groups H, C humanus and G, which causes the formation of specific antibodies in man. The identification of these antibodies in the human blood and and information on their concentration is of diagnostic importance, because an elevated concentration thereof indicates an existing or preceding streptococcal infection and may be a diagnosis hint to spondylarthrosis ankylopoietica (Bechterew's disease), glomerulonephritis, angina, scarlet fever, erysipelas, tonsillitis, pneumonia or sepsis caused by streptococci. Extremely low anti-streptolysin O titer values have been found in the case of nephrosis and hypogammaglobulinemia.

Latex agglutination tests for the determination of anti-streptolysin O are already known. However, these known latex reagents are insufficiently stable under practice conditions; their sensitivity may rapidly decrease or increase.

Surprisingly, a process has now been found which allows the preparation of a stable latex reagent for the determination of anti-streptolysin O, according to which streptolysin O is reacted with a bifunctional low molecular weight compound and optionally a gamma globulin or a Fab fragment thereof, and the product is adsorbed to a latex according to known methods.

Subject of the invention is therefore a process for the preparation of a latex reagent for the determination of antibodies directed against streptolysin O, wherein streptolysin O is reacted with a bifunctional low molecular weight compound and optionally a gamma globulin or a Fab fragment thereof, and the product is adsorbed to a carrier, preferably a latex, according to known methods. Subject of the invention is furthermore a formulation which contains such a reagent.

The linkage of streptolysin O to a gamma globulin or the Fab part thereof does not alter the linkage properties for the corresponding antibody. The products are suitable for the preparation of a stable latex reagent. Gamma globulins appropriate in accordance with the invention are animal gamma globulins such as bovine gamma globulin, the Fab fragments thereof, or Fab fragments of human gamma globulin.

Suitable bifunctional compounds are those which form bonds with functional groups in proteins. Preferred are dialdehydes, bis-oxiranes, amino-vinylsulfones, bis-diazonium salts or water-soluble carbo-diimides of the formulae $$OHC-(CH_2)_n-CHO$$
$$n = 2-4$$

anion$^-$ $^+N_2-C_6H_4-NH-C_6H_4-N_2^+$ anion$^-$

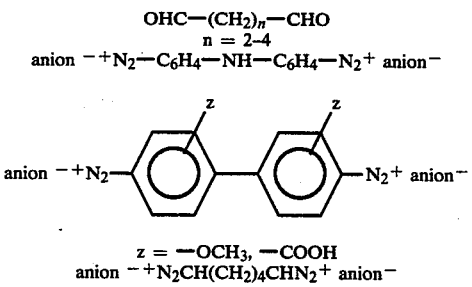

$$z = -OCH_3, -COOH$$
anion$^-$ $^+N_2CH(CH_2)_4CHN_2^+$ anion$^-$

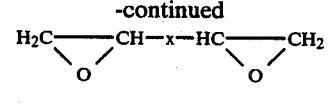

$$x = -CH_2, -OCH_2-CH_2-CH_2O-$$

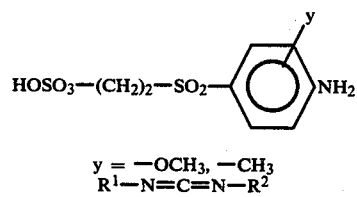

$$y = -OCH_3, -CH_3$$
$$R^1-N=C=N-R^2$$

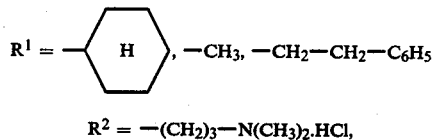

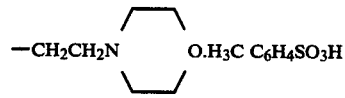

$$R^2 = -(CH_2)_3-N(CH_3)_2.HCl,$$

$-CH_2CH_2N\begin{pmatrix}\phantom{x}\\\phantom{x}\end{pmatrix}O.H_3C\ C_6H_4SO_3H$ Particularly preferred is glutaric dialdehyde.

The reactants can be contacted with one another in any sequence.

Preferred processes are as follows:

For preparing a product of streptolysin, gamma globulin or the Fab fragment thereof and bifunctional reagent, 1 to 10 parts by weight of bifunctional reagent are added to the gamma globulin or Fab fragment, and the mixture is stirred for 2 to 5 hours at pH 7–10 and a temperature of 0° to 20° C. The excess reagent is separated, glutaric dialdehyde preferably by means of a Sephadex ®G 25 or G 50 column, and the product is reacted at pH 7–10 and a temperature of 0° to 30° C. with 1 to 5 parts by weight of streptolysin O.

Especially advantageous is a "one-step" reaction, in which the components gamma globulin or Fab fragment and streptolysin O in a ratio of 1:0.1 to 1:10 are mixed with a bifunctional compound, and stirred for 1 to 10 hours at 0° to 20° C. In the case where the bifunctional compound is an aldehyde, the unreacted aldehyde groups can be bound in known manner with an amino acid, for example glycine.

The reaction product is mixed with a latex suspension in order to obtain the reagent of the invention.

Suitable latices are the known polymer latices, especially polystyrene latex.

The reagent obtained is most stable when reacting streptolysin O with a bifunctional reagent and a gamma globulin or a Fab fragment thereof. On the other hand, the stability is increased, too, when omitting the gamma globulin or Fab component in the reaction.

The reagent prepared according to the process of the invention is more stable than those of the state of the art not only at room temperature, but also at elevated temperature.

The following examples illustrate the invention.

EXAMPLE 1

10 g of streptolysin O and 2 g of the Fab fragment of a gamma globulin were mixed with 0.5 l of distilled water, and stirred. After about 30 minutes at 4° C., the streptolysin O was dissolved. It was centrifuged at 10,000 rpm, and the sediment was rejected. 4 ml of a 25% glutaric dialdehyde solution (w:v), dissolved in 900 ml of PBS (phosphate buffered saline solution), were added to the solution, and the batch was stirred for 5 hours at 4° C. 1 g of glycine was added to the conjugate, and the whole was stirred for a further 12-16 hours at the above temperature.

The latex reagent was prepared according to known methods. The conjugate was mixed with bovine or human albumin, and polystyrene latex was added until the intended sensitivity was attained, which was adjusted by means of dilutions of a standard. Anti-streptolysin O was detected in the blood by means of the latex reagent so prepared. It was furthermore applied for a semiquantitative determination of antibodies against streptolysin O in a vial according to known methods.

EXAMPLE 2

10 g of streptolysin O and 4 g of Fab fragment of a gamma globulin were mixed with 0.5 liter of distilled water, and stirred. After about 30 minutes at 4° C. the streptolysin O was dissolved. It was centrifuged at 10,000 rpm, and the sediment was rejected. 5 ml of a 25% glutaric dialdehyde solution dissolved in 800 ml of PBS were added to the solution, and the batch was stirred for 5 hours at 4° C. The excess glutaric dialdehyde was separated via a Sephadex G 50 column, and after concentration the conjugate was used for the preparation of latex ASL reagent.

EXAMPLE 3

5 g of streptolysin O were mixed with 250 ml of distilled water, and stirred. After 30 minutes at 4° C., the streptolysin O was dissolved. It was centrifuged at 10,000 rpm, and the sediment was rejected. 60 ml of a 25% glutaric dialdehyde solution (w:v) dissolved in 300 ml of PBS were added to the solution, and the batch was stirred for 2 hours at 4° C. The excess glutaric dialdehyde was separated via a Sephadex G 50 column. The eluate was concentrated to about 600 ml. 2 g of Fab fragment dissolved in 100 ml of PBS were added to the solution, and the batch was stirred for 12-16 hours at 4° C. 1 of glycine were added to the solution, and stirring was continued for a further 16 hours. The conjugate was used for the preparation of a latex reagent.

When in Example 1 the dialdehyde was replaced by 0.1 to 10 parts by weight of 1-amino-4-beta-oxethylsulfonic acid ester (parabase ester) or of 1-cyclogexyl-3(2morpholinoethyl)-carbo-diimide-p-toluenesulfonic acid, reagents having similar properties were obtained. The reaction conditions (pH, temperature) were adapted to the reagent used in each case.

EXAMPLE 4

2 g of the Fab fragment of a gamma globulin were dissolved in 80 ml of distilled water at +4° C. A mixture of 4 ml of a solution of 25 g of glutaric dialdehyde in 100 ml of water and of 1,500 ml of PBS (phosphate buffered saline solution) was added to the solution and the batch was stirred for 5 hours at +4° C. The excess glutaric dialdehyde was separated via a Sephadex G 50 column and the reaction product of the Fab fragment and glutaric dialdehyde was concentrated by ultrafiltration. 10 g of streptolysin O in 500 ml of PBS were added to the solution and the batch was stirred for 16 hours at +4° C. The conjugate was used for the preparation of latex ASL reagent.

EXAMPLE 5

2 g of the Fab fragment of a gamma globulin were dissolved at +4° C. in 150 ml of distilled water. A mixture of 2 ml of a solution of 25 g of glutaric dialdehyde in 100 ml of water and of 1,500 ml of PBS was added to the solution and the resultant solution was stirred for 5 hours at +4° C. 6 g of streptolysin O dissolved in 600 ml of distilled water containing 3.6 g of $MgSO_4.7H_2O$ were added and the mixture was stirred for 16 hours at +4° C. After concentration, the conjugate was used for the preparation of latex ASL reagent.

Reagents having similar properties were obtained when replacing dialdehyde in the preceding examples by 0.1 to 10 weight parts of 1-amino-4-beta-oxethylsulfonic acid ester (parabase ester) or of 1-cyclohexyl-3-(2-morpholinoethyl)carbo-diimide p-toluenesulfonic acid. The reaction conditions (pH, temperature) were adapted to the reagent used in each case.

What is claimed is:

1. A process for the preparation of an antistreptolysin O latex reagent, which comprises reacting streptolysin O with a bifunctional low molecular weight compound to form a product and adsorbing said product to latex particles.

2. A process for the preparation of an antistreptolysin O latex reagent, which comprises reacting streptolysin O with a bifunctional low molecular weight compound and with a compound selected from the group consisting of a gamma globulin and a Fab fragment of a gamma globulin to form a product and adsorbing said product to latex particles.

3. A process for the preparation of an antistreptolysin O latex reagent, which comprises reacting a Fab fragment of a gamma globulin with a bifunctional low molecular weight compound, separating any excess or unreacted bifunctional low molecular weight compound, adding streptolysin O, and adsorbing the product to latex particles.

4. The process as recited in claim 1, 2, or 3, wherein said latex particles are polystyrene homopolymer particles.

5. The antistreptolysin O latex reagent produced according to claim 4.

6. The process as recited in claim 1, 2, or 3, wherein said latex particles are polystyrene copolymer particles.

7. The antistreptolysin O latex reagent produced according to claim 6.

8. The process as recited in claim 1 or 2, wherein said gamma globulin is human gamma globulin.

9. The antistreptolysin O latex reagent produced according to claim 8.

10. The process as recited in claim 1 or 2, wherein said Fab fragment is the Fab fragment of human gamma globulin.

11. The antistreptolysin O latex reagent produced according to claim 10.

12. The process as recited in claim 1 or 2, wherein said gamma globulin is bovine gamma globulin.

13. The antistreptolysin O latex reagent produced according to claim 12.

14. The process recited in claim 1 or 2, wherein said Fab fragment is the Fab fragment of a bovine gamma globulin.

15. The antistreptolysin O latex reagent produced according to claim 14.

16. The process as recited in claim 1, 2, or 3, wherein said bifunctional compound is a compound selected from the group consisting of compounds of the following formulae:

OHC—(CH$_2$)$_n$—CHO wherein n = 2–4

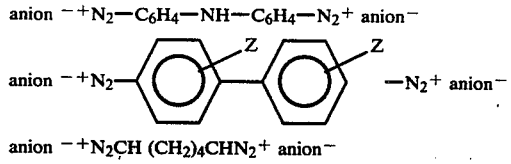

wherein z = —OCH$_3$ or —COOH

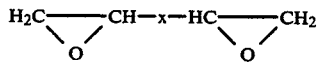

wherein x = —CH$_2$ or —OCH$_2$—CH$_2$—CH$_2$O—

HOSO$_3$—(CH$_2$)$_2$—SO$_2$— 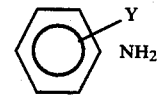

wherein y = —OCH$_3$ or —CH$_3$

R$^1$—N=C=N—R$^2$ wherein R$^1$ =

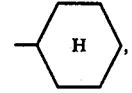

—CH$_3$, or —CH$_2$—CH$_2$—C$_6$H$_5$ and R$^2$ = —(CH$_2$)$_3$—N(CH$_3$)$_2$.HCl or

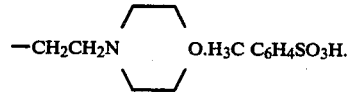

17. The antistreptolysin O latex reagent produced according to claim 16.
18. The process as recited in claim 1, 2, or 3, wherein said bifunctional compound is glutaric dialdehyde.
19. The antistreptolysin O latex reagent produced according to claim 18.
20. The antistreptolysin O latex reagent produced according to claim 1, 2, or 3.

* * * * *

UNITED STATES PATENT AND TRADEMARK OFFICE
CERTIFICATE OF CORRECTION

PATENT NO. : 4,508,831
DATED : April 2, 1985
INVENTOR(S) : Tibor Toth

It is certified that error appears in the above-identified patent and that said Letters Patent is hereby corrected as shown below:

Claims 8, 10, 12 and 14, line 1, "recited in claim 1 or 2" should be --recited in claim 2 or 3--.

Signed and Sealed this

Twenty-third Day of July 1985

[SEAL]

Attest:

DONALD J. QUIGG

Attesting Officer  Acting Commissioner of Patents and Trademarks